(12) United States Patent
Chakrabarti et al.

(10) Patent No.: US 11,072,587 B2
(45) Date of Patent: Jul. 27, 2021

(54) ADMINISTRATION OF AURORA KINASE INHIBITORS FOR ANTI-MALARIAL THERAPY

(71) Applicant: University of Central Florida Research Foundation, Inc., Orlando, FL (US)

(72) Inventors: Debopam Chakrabarti, Winter Springs, FL (US); Ratna Chakrabarti, Winter Springs, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 0 days.

(21) Appl. No.: 16/126,645

(22) Filed: Sep. 10, 2018

(65) Prior Publication Data

US 2019/0077768 A1 Mar. 14, 2019

Related U.S. Application Data

(60) Provisional application No. 62/555,696, filed on Sep. 8, 2017.

(51) Int. Cl.
| | |
|---|---|
| *C07D 239/38* | (2006.01) |
| *A61P 33/06* | (2006.01) |
| *C07D 401/14* | (2006.01) |
| *C07D 417/14* | (2006.01) |
| *C07D 413/12* | (2006.01) |
| *C07D 413/14* | (2006.01) |
| *C07D 417/12* | (2006.01) |
| *C07D 403/12* | (2006.01) |

(52) U.S. Cl.
CPC ............ *C07D 239/38* (2013.01); *A61P 33/06* (2018.01); *C07D 401/14* (2013.01); *C07D 403/12* (2013.01); *C07D 413/12* (2013.01); *C07D 413/14* (2013.01); *C07D 417/12* (2013.01); *C07D 417/14* (2013.01)

(58) Field of Classification Search
CPC .................................................... C07D 239/38
USPC ......................................................... 546/193
See application file for complete search history.

(56) References Cited

FOREIGN PATENT DOCUMENTS

RU    WO 2012169934    * 12/2012    ........... C07D 417/12

OTHER PUBLICATIONS

Berry, Cellular Microbiology (2016), 18(8), 1106-1120.*
Dichiara et al. ChemMedChem2017,12,1235-1253.*
Vasilevich, Chemical Biology & Drug Design (2016), 88(1), 54-65.*
Vasilevich1, Pharmaceuticals (2016), 9(2), 19/1-19/14.*
Baron, Medical Microbiology, 4th edition, Galveston (TX): University of Texas Medical Branch at Galveston; 1996, Crutcher, in Chapter 83.*
Reininger, Molecular Microbiology (2011), 79(1), 205-221.*
Johnson, J.D., et al., Assessment and continued validation of the malaria SYBR green I-based fluorescence assay for use in malaria drug screening. Antimicrob Agents Chemother, 2007. 51(6): p. 1926-33.
Malich, G., B. Markovic, and C. Winder, The sensitivity and specificity of the MTS tetrazolium assay for detecting the in vitro cytotoxicity of 20 chemicals using human cell lines. Toxicology, 1997. 124(3): p. 179-92.

* cited by examiner

*Primary Examiner* — Nizal S Chandrakumar
(74) *Attorney, Agent, or Firm* — Timothy H. Van Dyke; Wolter Van Dyke Davis, PLLC

(57) ABSTRACT

Novel compositions and methods for the treatment and prevention of malaria are disclosed herein.

4 Claims, 19 Drawing Sheets

Compound 001 (LAS 31077790)

- Dd2 IC50: 82.5nM
- HepG2 IC50: 233.9nM
- 3T3 IC50: 1754nM
- Selectivity: 2.8/21.3

Compound 002 (LAS 31077836)

- Dd2 IC50: 124.8nM
- HepG2 IC50: 539.7nM
- 3T3 IC50: 530.9nM
- Selectivity: 4.3

Compound 003 (LAS 29955976)

- Dd2 IC50: 351.8nM
- HepG2 IC50: 2174nM
- Selectivity: 6.2

Compound 004 (LAS 28819538)

- Dd2 IC50: 1287.8nM
- HepG2 IC50: 3840nM
- Selectivity: 3.0

Compound 005 (LAS 29746229)

- Dd2 IC50: 860.9nM
- HepG2 IC50: 3480nM
- Selectivity: 4.0

Compound 006 (LAS 32174756)

- Dd2 IC50: 507.8nM
- HepG2 IC50: 6977nM
- Selectivity: 13.7

Compound 007 (LAS 29955974)

- Dd2 IC50: 701.1nM
- HepG2 IC50: 5262nM
- Selectivity: 7.5

Compound 101 (Alisertib)

- Dd2 IC50: 2408.1nM

Compound 102 (Barasertib)
- Dd2 IC50: 198.8nM

Compound 103 (MK-5108)
- Dd2 IC50: 5039.4nM

Compound 104 (Danusertib)

- Dd2 IC50: 418.9nM

Compound 105 (Tozasertib)

- Dd2 IC50: 1580.2nM

Compound 106 (ZM-447439)

- Dd2 IC50: 103nM
- HepG2 IC50: 610.5nM
- Selectivity: 5.9 a
ADMINISTRATION OF AURORA KINASE INHIBITORS FOR ANTI-MALARIAL THERAPY

FIELD

The present disclosure relates to novel anti-malarial compounds and methods for their use.

BACKGROUND

Malaria is an infectious disease caused by a microorganism of the genus *Plasmodium*. Upon infection, the parasites (sporozoites) travel to the liver where they mature and release another form of parasites called merozoites. The parasites enter the bloodstream and multiply inside red blood cells, which then break open and infect more red blood cells. Malaria may be treated with oral medications such as chloroquine, quinine sulfate, hydroxychloroquine, mefloquine, atovaquone, and/or proguanil amongst other agents. It is known that these malarial parasites may evolve and become resistant to the administered medications. In many cases, the parasite is able to survive and continue to multiply despite being targeted with anti-malarial compounds.

DETAILED DESCRIPTION

Figure 1:
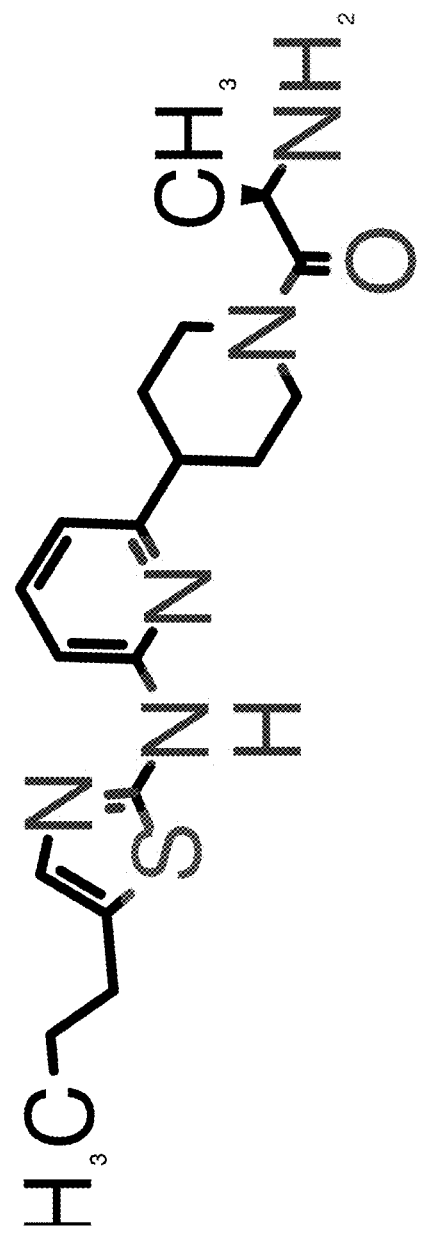
FIG. 1 Provides a diagram showing the structure of an aurora kinase inhibitor compound 1.
Figure 2:
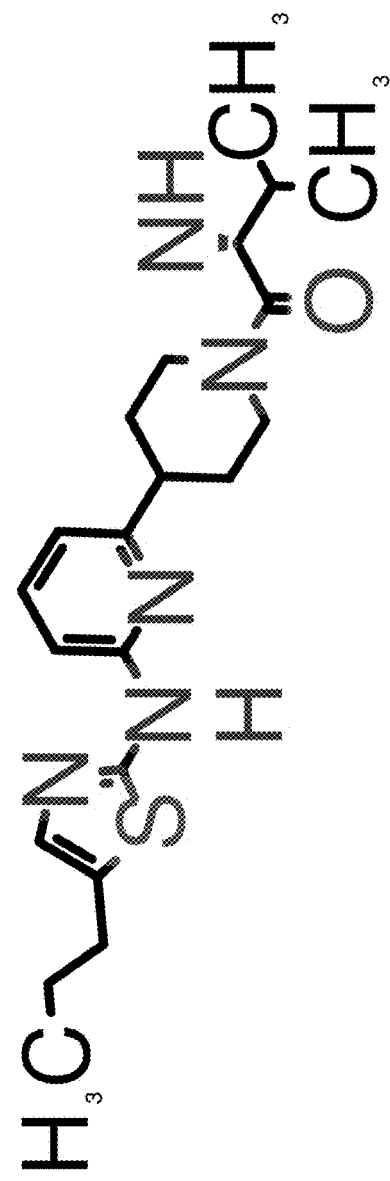
FIG. 2 Provides a diagram showing the structure of an aurora kinase inhibitor compound 2.
Figure 3:
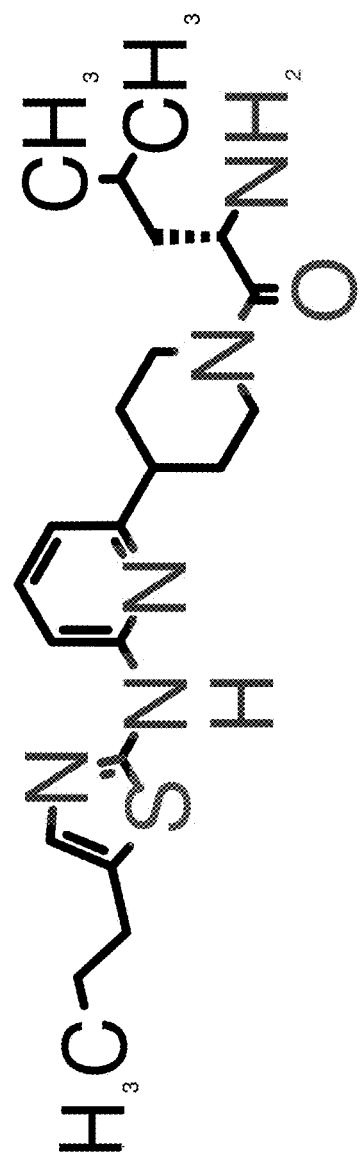
FIG. 3 Provides a diagram showing the structure of an aurora kinase inhibitor compound 3.
Figure 4:
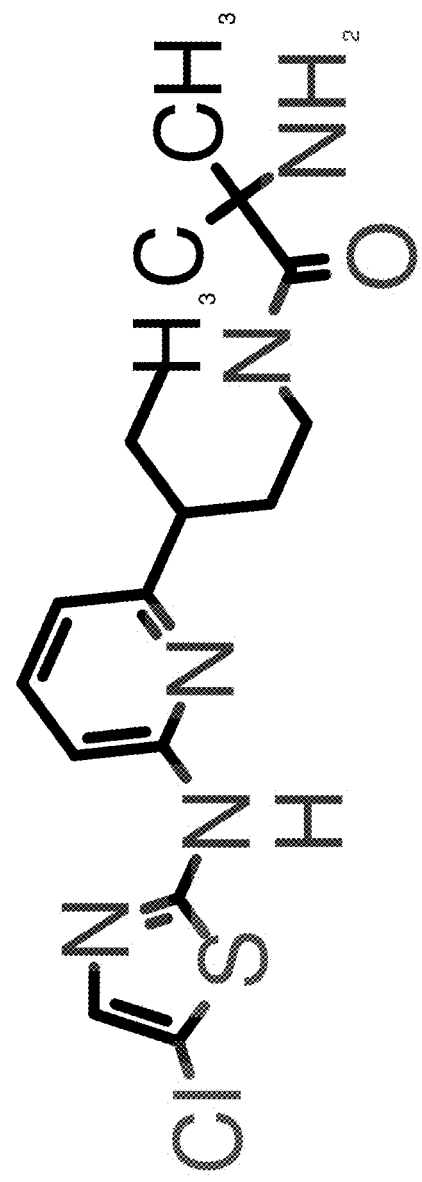
FIG. 4 Provides a diagram showing the structure of an aurora kinase inhibitor compound 4.
Figure 5:
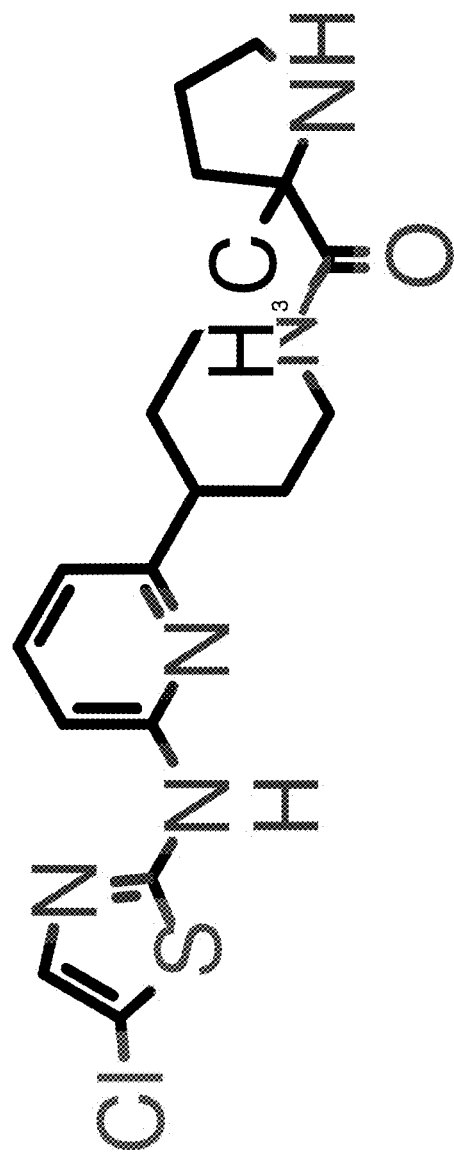
FIG. 5 Provides a diagram showing the structure of an aurora kinase inhibitor compound 5.
Figure 6:
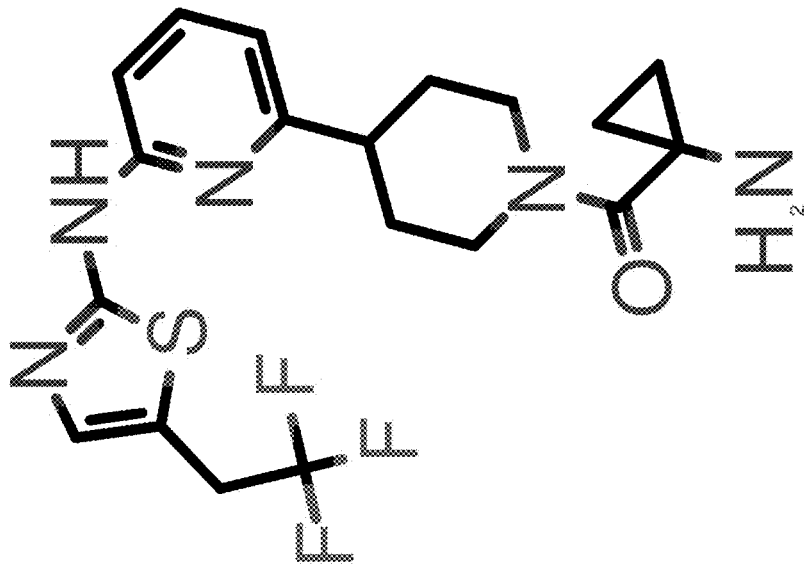
FIG. 6 Provides a diagram showing the structure of an aurora kinase inhibitor compound 6.
Figure 7:
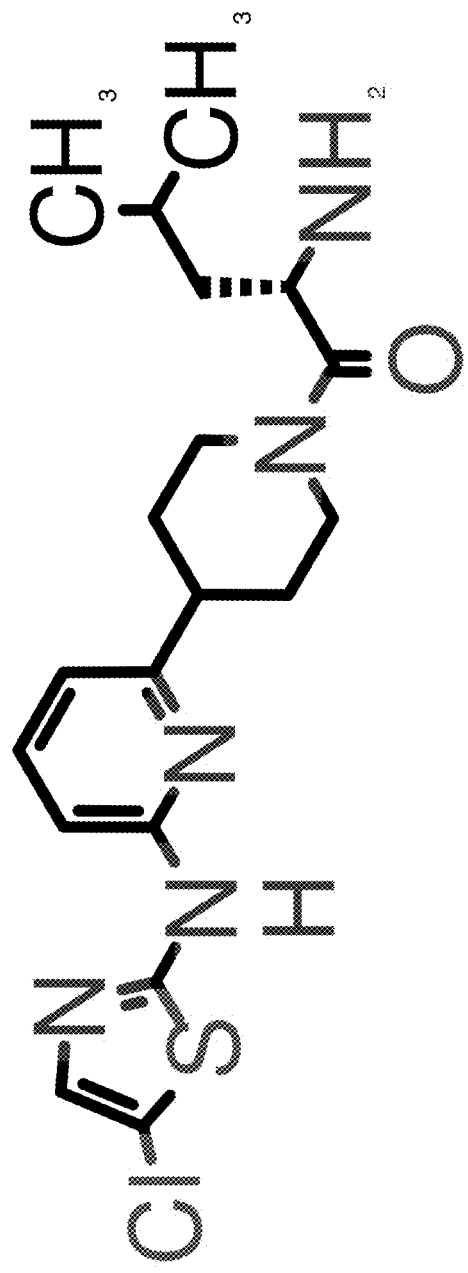
FIG. 7 Provides a diagram showing the structure of an aurora kinase inhibitor compound 7.
Figure 8:
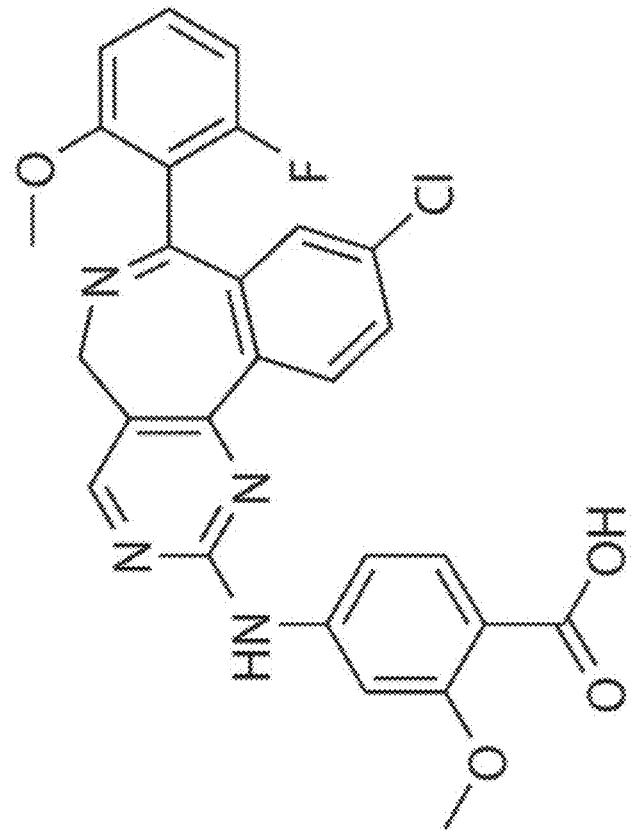
FIG. 8 Provides a diagram showing the structure of an aurora kinase inhibitor compound 101.
Figure 9:
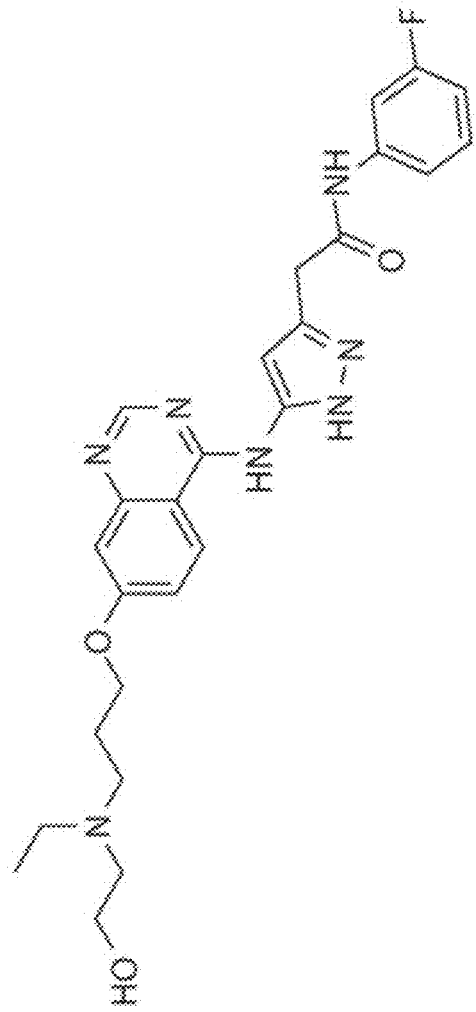
FIG. 9 Provides a diagram showing the structure of an aurora kinase inhibitor compound 102.
Figure 10:
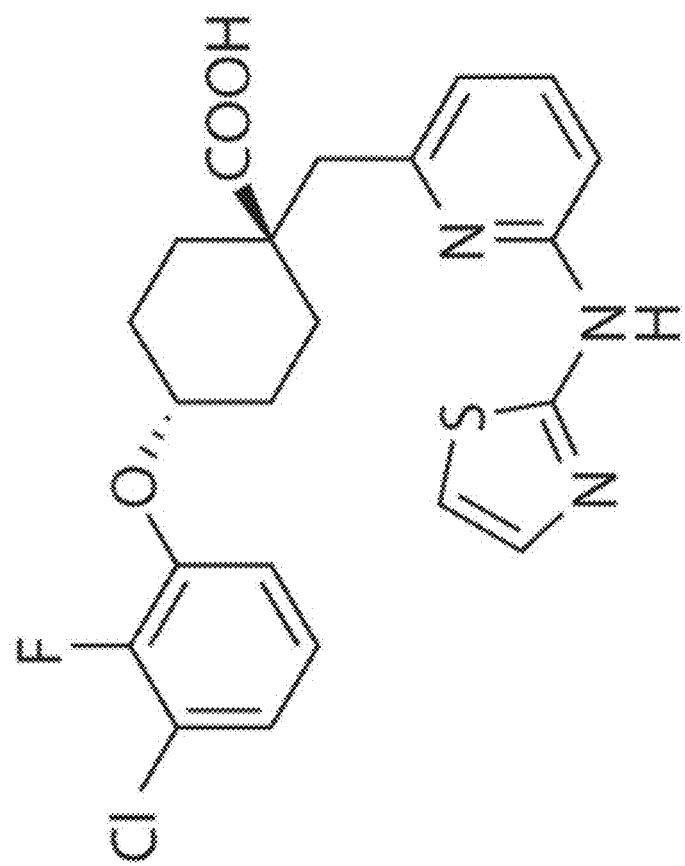
FIG. 10 Provides a diagram showing the structure of an aurora kinase inhibitor compound 103.
Figure 11:
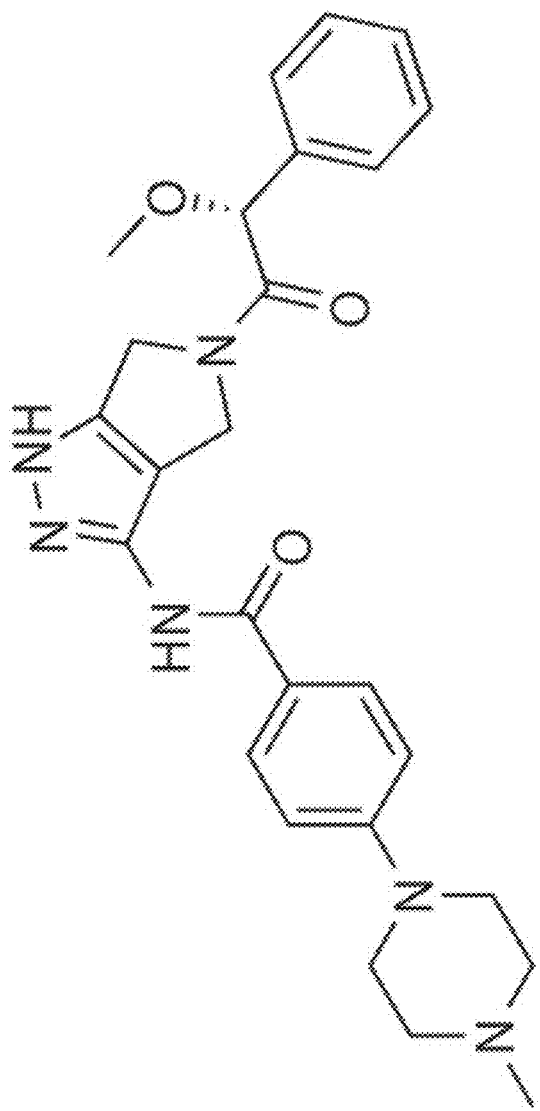
FIG. 11 Provides a diagram showing the structure of an aurora kinase inhibitor compound 104.
Figure 12:
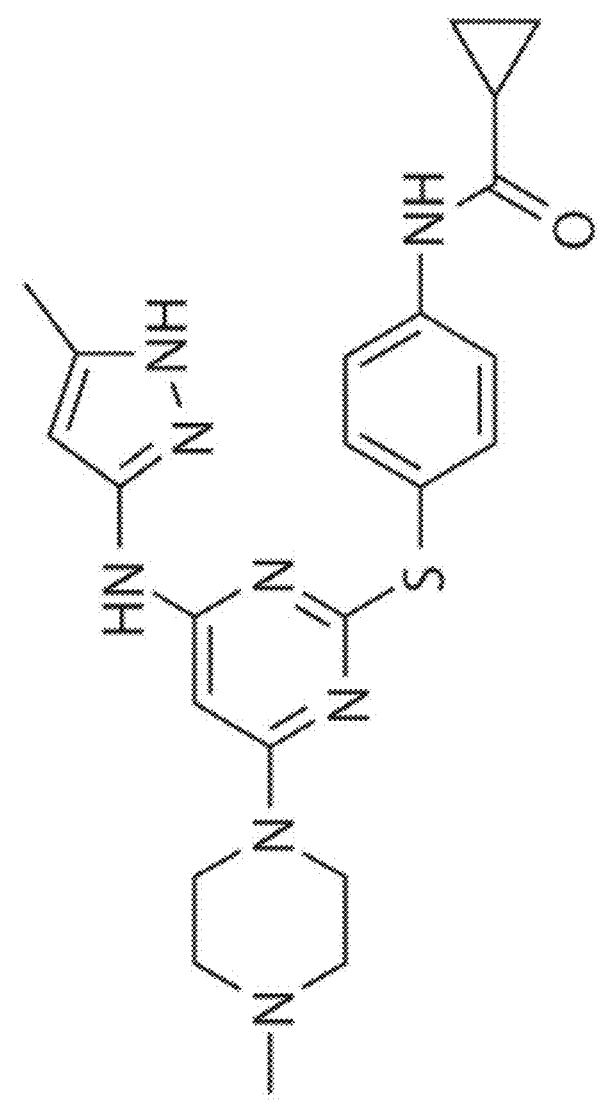
FIG. 12 Provides a diagram showing the structure of an aurora kinase inhibitor compound 105.
Figure 13:
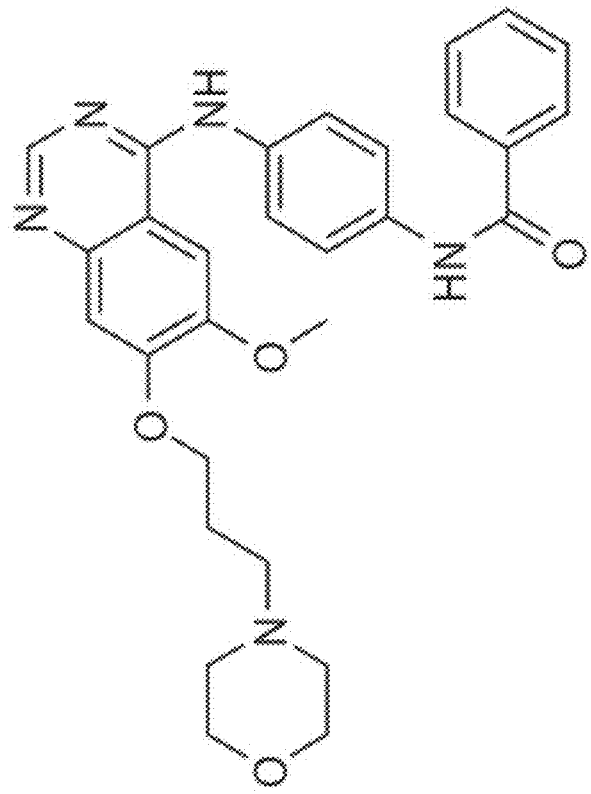
FIG. 13 Provides a diagram showing the structure of an aurora kinase inhibitor compound 106.
Figure 14:
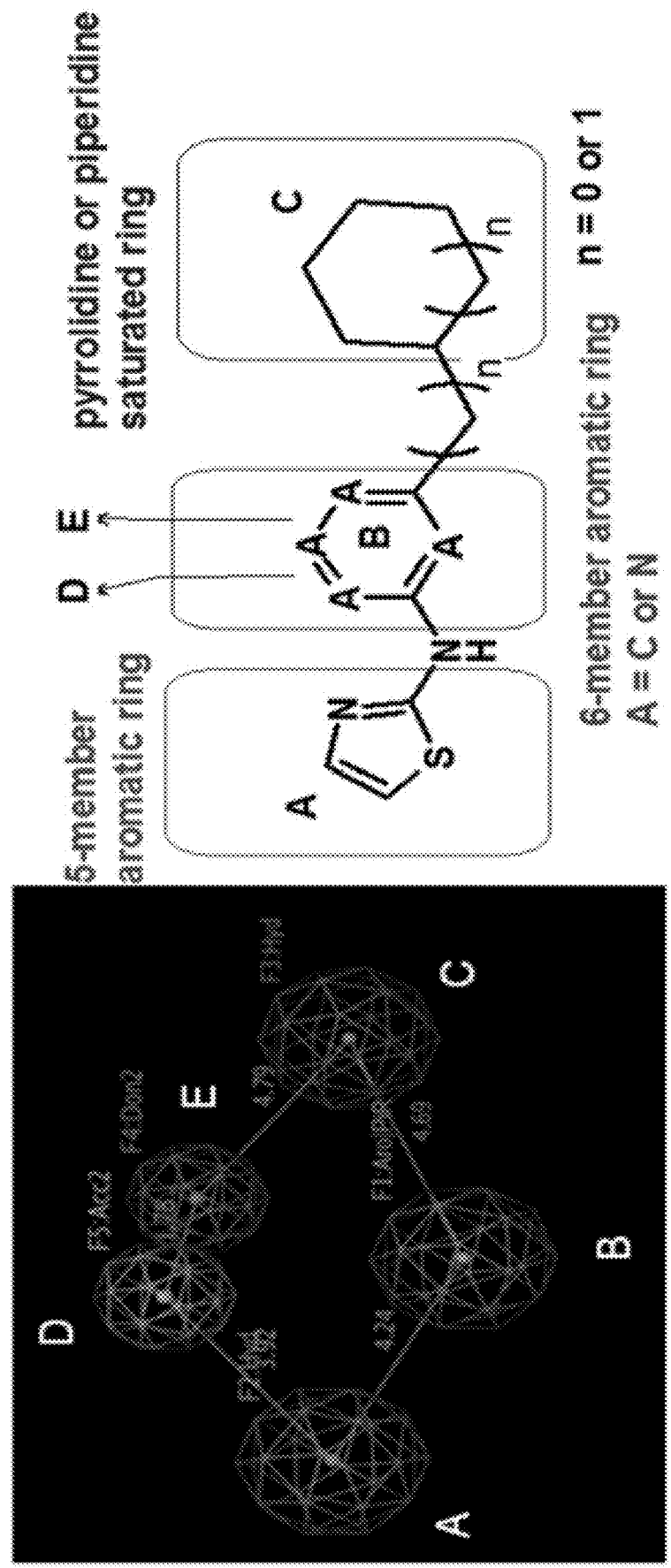
FIG. 14 Provides a diagram showing a pharmacophore formula of anti-malarial compound embodiments.

The present disclosure is directed to use of aurora kinase inhibitors as anti-malarial agents. These compounds have structures different from current anti-malarial compounds. Aurora kinase is a novel target for treating malaria, which may alleviate the problem of drug resistance. According to certain embodiments, the disclosure provides methods of treating or preventing malarial infection involving the administration of aurora kinase inhibitors taught herein to a subject in need. In one embodiment, the anti-malarial compound includes a compound encompassed by the following formula:

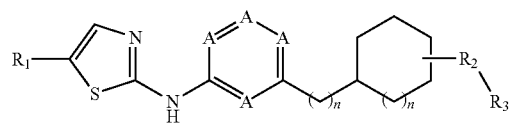

Wherein A=C or N; n=0 or 1;

$R_1$=hydrogen; hydroxy, halo, haloalkyl, thiocarbonyl, alkoxy, alkenoxy, alkylaryloxy, aryloxy, arylalkyloxy, cyano; nitro; imino; alkylamino; aminoalkyl; thio; sulfhydryl; thioalkyl; alkylthio; sulfonyl; C1-C6 straight or branched chain alkyl; $C_2$-$C_6$ straight or branched chain alkenyl or alkynyl; aryl; aralkyl; heteroaryl; carbocycle or heterocycle group or moiety; or $CO_2R_4$ where $R_4$ is hydrogen or $C_1$-$C_9$ straight or branched chain alkyl or $C_2$-$C_9$ straight or branched chain alkenyl group or moiety; substituted straight $C_1$-$C_6$ alkyl chain; or substituted branched $C_1$-$C_6$ alkyl chain;

$R_2$=Carbon, Sulfur, or Nitrogen;

R3=H, $CH_3$, $NH_2$, or

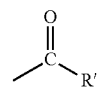

wherein R' is H, Carboxyl, or one of A-F:

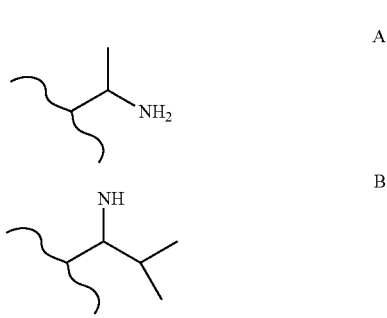

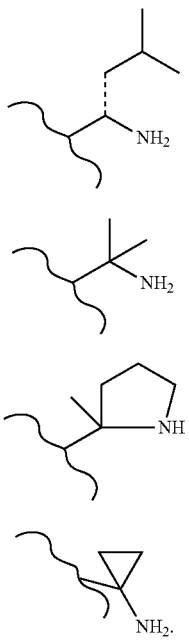

In a specific embodiment, $R_1$ is 3 carbon straight alkyl chain.
In a more specific embodiment, when $R_1$ is 3 carbon straight alkyl chain, R' is A, B, or C.
In another specific embodiment, $R_1$ is Cl. In a more specific embodiment, when $R_1$ is Cl, R' is D or E.
In another specific embodiment, $R_1$ is (F being fluorine)

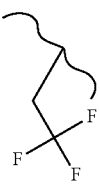

In a more specific embodiment, when $R_1$ is (F being fluorine)

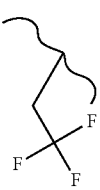

R' is F (as set forth above for R').

Definitions

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. Prior to setting forth the invention in detail and for purposes of more clearly facilitating an understanding the invention as disclosed and claimed herein, the following definitions are provided.

As used herein, the terms "about" and "approximately" as used herein refers to—values that are ±10% of the stated value.

As used herein, the terms "administering" or "administration" of a composition as described herein to a subject includes any route of introducing or delivering to a subject a compound to perform its intended function. The administering or administration can be carried out by any suitable route, including orally, intranasally, parenterally (intravenously, intramuscularly, intraperitoneally, or subcutaneously), rectally, or topically. Administering or administration includes self-administration and the administration by another.

As used herein, the term "analog" refers to a compound having a structure similar to that of another one, but differing from it with respect to a certain component. The compound may differ in one or more atoms, functional groups, or substructures, which may be replaced with other atoms, groups, or substructures. In one aspect, such structures possess at least the same or a similar therapeutic efficacy.

As used herein, "anti-malarial" or "anti-malarial activity" includes any activity that decreases the infectivity, the reproduction, or inhibits the progress of the lifecycle of a malaria parasite. "Anti-malarial activity" includes inhibition of the growth of malaria infection by all of the means of observed with current anti-malarial drugs.

As used herein, the term "aurora kinase inhibitor" refers to any compound that reduces the activity of or expression of aurora kinase. In particular embodiments, aurora kinase inhibitors are designated by compounds 1, 2, 3, 4, 5, 6, 7, 101, 102, 103, 104, 105, 106, DC-5156, DC-5154 and DC-5146 as set forth herein and illustrated in FIGS. 1-13, and 16, and any combinations, prodrugs, pharmaceutically acceptable salts, analogs, and derivatives thereof.

As used herein, "derivative" refers to a compound derived or obtained from another and containing essential elements of the parent compound. In one aspect, such a derivative possesses at least the same or similar therapeutic efficacy as the parent compound.

As used herein, by the term "effective amount" "amount effective," or the like, it is meant an amount effective at dosages and for periods of time necessary to achieve the desired result.

As used herein, the term "malaria" refers to an infectious disease spread by mosquitoes and caused by parasites of the genus *Plasmodium*.

As used herein, the term "parasite" refers to microorganisms that generally exploit the resources of its host body. Parasites may show a high degree of specialization and reproduce faster than their host. Parasites may also kill or reduce the biological mechanisms of the hosts.

As used herein, the term "pharmaceutically acceptable salt" is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

As used herein, the term "preventing" means causing the clinical symptoms of the disease state not to worsen or develop, e.g., inhibiting the onset of disease, in a subject that may be exposed to or predisposed to the disease state, but does not yet experience or display symptoms of the full disease state, e.g., malaria.

As used herein, the term "prodrug" refers to a compound that is converted to a therapeutically active compound after administration, and the term should be interpreted as broadly herein as is generally understood in the art. Generally, but not necessarily, a prodrug is inactive or less active than the therapeutically active compound to which it is converted.

As used herein, the term "stereoisomer" refers to a compound which has the identical chemical constitution, but differs with regard to the arrangement of the atoms or groups in space.

As used herein, the term "subject" refers to any animal (e.g., a mammal), including, but not limited to, humans, which may be the recipient of a particular treatment.

As used herein, the terms "treating" or "treatment" or "alleviation" refers to both therapeutic treatment and prophylactic or preventative measures, wherein the objective is to prevent or slow down (lessen) the targeted pathologic condition or disorder.

Derivatives

According to certain embodiments, as used herein, derivatives of aurora kinase inhibitors include salts, esters, enol ethers, enol esters, acetals, ketals, orthoesters, hemiacetals, hemiketals, solvates, hydrates, metabolites or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, alk(en)(yn)yl, aryl, aralkyl, and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, alk(en)(yn)yl, aryl, aralkyl, or cycloalkyl. Pharmaceutically acceptable enol esters include, but are not limited to, derivatives of formula C=C(OC(O)R) where R is hydrogen, alkyl, alkenyl, alkynyl, aryl, aralkyl, or cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

According to further embodiments, derivatives may include, but are not limited to, specific substitutions of reactive constituents on or emanating from an aurora kinase inhibitor found in FIGS. 1-13, 14, and 16, and may include, but are not limited to, one or more of the following: a hydrogen, hydroxy, halo, haloalkyl, thiocarbonyl, alkoxy, alkenoxy, alkylaryloxy, aryloxy, arylalkyloxy, cyano, nitro, imino, alkylamino, aminoalkyl, thio, sulfhydryl, thioalkyl, alkylthio, sulfonyl, C1-C6 straight or branched chain alkyl, C2-C6 straight or branched chain alkenyl or alkynyl, aryl, aralkyl, heteroaryl, carbocycle, or heterocycle group or moiety, or CO2R7 where R7 is hydrogen or C1-C9 straight or branched chain alkyl or C2-C9 straight or branched chain alkenyl group or moiety.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, alkyl refers to an unbranched or branched hydrocarbon chain. An alkyl group may be unsubstituted or substituted with one or more heteroatoms.

As used herein, alkenyl refers to an unbranched or branched hydrocarbon chain comprising one or more double bonds. The double bond of an alkenyl group may be unconjugated or conjugated to another unsaturated group. An alkenyl group may be unsubstituted or substituted with one or more heteroatoms.

As used herein, alkynyl refers to an unbranched or branched hydrocarbon chain comprising one of more triple bonds therein. The triple bond of an alkynyl group may be unconjugated or conjugated to another unsaturated group. An alkynyl group may be unsubstituted or substituted with one or more heteroatoms.

As used herein, alk(en)(yn)yl refers to an unbranched or branched hydrocarbon group comprising at least one double bond and at least one triple bond. The double bond or triple bond of an alk(en)(yn)yl group may be unconjugated or conjugated to another unsaturated group. An alk(en)(yn)yl group may be unsubstituted or substituted with one or more heteroatoms.

Exemplary alkyl, alkenyl, alkynyl, and alk(en)(yn)yl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl (propynyl).

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl or isoquinolinyl.

As used herein, "halo," "halogen," or "halide" refers to F, Cl, Br or I.

As used herein, base refers to any compound that accepts protons in water or solvent. Thus, exemplary bases include, but are not limited to, alkali metal hydroxides and alkali metal alkoxides (i.e., MOR, wherein M is an alkali metal such as but not limited to potassium, lithium, or sodium and R is hydrogen, alkyl, alkenyl, alkynyl, or alk(en)(yn)yl) such as but not limited to potassium hydroxide, potassium tert-butoxide, potassium tert-pentoxide, sodium hydroxide, sodium tert-butoxide, lithium hydroxide, etc.); other hydroxides such as but not limited to magnesium hydroxide (Mg(OH)2), calcium hydroxide (Ca(OH)2), or barium hydroxide (Ba(OH)2); alkali metal hydrides (i.e., MH, wherein M is as defined above) such as but not limited to sodium hydride, potassium hydride, or lithium hydride; carbonates such as but not limited to potassium carbonate (K2O03), sodium carbonate (Na2CO3), potassium bicarbonate (KHCO3), or sodium bicarbonate (NaHCO$_3$); alkyl ammonium hydroxides, alkenyl ammonium hydroxides, alkynyl ammonium hydroxides, or alk(en)(yn)yl ammonium hydroxides such as but not limited to n-tetrabutyl ammonium hydroxide (TBAH); amines such as ammonia, diethylamine, 2,2,6,6-tetramethyl piperidine (HTMP), tertiary amines (such as but not limited to dimethylethyl amine, diisopropylethylamine, trimethylamine, triethylamine, tributylamine, N-methylmorpholine, N-methylpyrrolidine, 1,8-diazabicyclo[5.4.0]-7-undecene (DBU), 1,5-diazabicyclo[4.3.0]-5-nonene (DBN), or tetramethylenediamine (TMEDA)), aromatic amines (such as but not limited to pyridine, collidine, lutidine, picoline, quinoline, or N,N-dimethylaniline); alkali metal amides such as but not limited to lithium amide, lithium dimethylamide, lithium diisopropylamide (LDA), lithium tetramethylpiperidide (LiTMP), or alkali metal hexamethyldisilazanes (such as but not limited to potassium hexamethyldisilazane, (KHMDS), sodium hexamethyldisilazane (NaH MDS), or lithium hexamethyldisilazane (LiHMDS)); alkyl lithiums, alkenyl lithiums, alkynyl lithiums, or alk(en)(yn)yl lithiums such as but not limited to n-butyl lithium sec-butyllithium, isopropyllithium; alkyl magnesium halides, alkenyl magnesium halides, alkynyl magnesium halides, or alk(en)(yn)yl magnesium halides such as but not limited to methyl magnesium bromide.

As used herein, solvent refers to any liquid that completely or partially dissolves a solid, liquid, or gaseous solute, resulting in a solution such as but not limited to hexane, benzene, toluene, diethyl ether, chloroform, ethyl acetate, dichloromethane, carbon tetrachloride, 1,4-dioxane, tetrahydrofuran, glyme, diglyme, acetone, acetonitrile, dimethylformamide, dimethyl sulfoxide, dimethylacetamide, or N-methyl-2-pyrrolidone.

As used herein, dehydrating agent refers to any compound that promotes the formation of carboxamides from carboxylic acids, such as but not limited to thionyl chloride, sulfuryl chloride, a carbodiimide, an anhydride or a mixed anhydride, a phenol (such as but not limited to nitrophenol, pentafluorophenol, or phenol), or a compound of Formula (A):

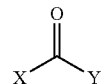

(A)

wherein each of X and Y is independently an unsubstituted or substituted heteroaryl group (such as but not limited to imidazolyl, benzimidazolyl, or benzotriazolyl). Examples of dehydrating agents further include, but are not limited to, benzotriazole-1-yl-oxy-tris-(dimethylamino)-phosphonium hexafluorophosphate (BOP), N,N'-carbonyldiimidazole (CDI), 3-(diethoxyphosphoryloxy)-1,2,3-benzotriazin-4 (3H)-one (DEPBT), 1-ethyl-3-(3-dimethylaminopropyl) carbodiimide (EDC), 2-(7-aza-1H-benzotriazole-1-yl)-1,1, 3,3-tetramethyluronium hexafluorophosphate (HATU), 2-(1H-benzotriazole-1-yl)-1,1,3,3-tetramethyluronium hexafluorophosphate (HBTU), 1-hydroxybenzotriazole (HOBt), benzotriazole-1-yl-oxy-tris-pyrrolidino-phosphonium hexafluorophosphate (PyBOP), 2-(1H-benzotriazole-1-yl)-1,1,3,3-tetramethyluronium tetrafluoroborate (TBTU), O-(3,4-dihydro-4-oxo-1,2,3-benzotriazine-3-yl)-N,N,N,N-tetra methyluronium tetrafluoroborate (TDBTU), 3-(diethyloxyphosphoryloxy)-1,2,3-benzotriazin-4(3H)-one (DEPBT), dicyclohexylcarbodiimide (DCC), N,N'-diisopropylcarbodiimide (DIC), or 1-hydroxy-7-azabenzotriazole (HOAt).

As used herein, acid refers to any compound that contains hydrogen and dissociates in water or solvent to produce positive hydrogen ions, as well as Lewis acids, including but not limited to hydrochloric acid, sulfuric acid, phosphoric acid, acetic acid, trihaloacetic acids (such as but not limited to trifluoroacetic acid or trichloroacetic acid), hydrogen bromide, maleic acid, sulfonic acids (such as but not limited to toluenesulfonic acids or camphorsulfonic acids), propionic acids (such as but not limited to (R)-chloropropionic acid), phthalamic acids (such as but not limited to N—[(R)-1-(1-naphthyl)ethyl]phthalamic acid), tartaric acids (such as but not limited to L-tartaric acid or dibenzyl-L-tartaric acid), lactic acids, camphoric acids, aspartic acids, or citronellic acids.

It is to be understood that reactants, compounds, solvents, acids, bases, catalysts, agents, reactive groups, or the like may be added individually, simultaneously, separately, and in any order. Furthermore, it is to be understood that reactants, compounds, acids, bases, catalysts, agents, reactive groups, or the like may be pre-dissolved in solution and added as a solution (including, but not limited to, aqueous solutions). In addition, it is to be understood that reactants, compounds, solvents, acids, bases, catalysts, agents, reactive groups, or the like may be in any molar ratio.

It is to be understood that reactants, compounds, solvents, acids, bases, catalysts, agents, reactive groups, or the like may be formed in situ.

Enantiomers/Tautomers

Aurora kinase inhibitors of the disclosure also include where appropriate all enantiomers and tautomers of the agents, such as those disclosed in FIGS. 1-13 and novel agents referred to herein. One skilled in the art will recognize compounds that possess optical properties (one or more chiral carbon atoms) or tautomeric characteristics. The corresponding enantiomers and/or tautomers may be isolated/prepared by methods known in the art.

Stereo and Geometric Isomers

Aurora kinase inhibitors of the disclosure, such as those disclosed in FIGS. 1-13 and novel agents referred to herein, may exist as stereoisomers and/or geometric isomers—e.g. they may possess one or more asymmetric and/or geometric centres and so may exist in two or more stereoisomeric and/or geometric forms. Contemplated herein is the use of all the individual stereoisomers and geometric isomers of those inhibitor agents, and mixtures thereof. The terms used in the claims encompass these forms, provided said forms retain the appropriate functional activity (though not necessarily to the same degree).

Anti-malarial agents of the disclosure also include all suitable isotopic variations of the agent or pharmaceutically acceptable salts thereof. An isotopic variation of an anti-malarial agent or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as 2H, 3H, 13C, 14C, 15N, 17O, 18O, 31P, 32P, 35S, 18F and 36Cl, respectively. Certain isotopic variations of the agent and pharmaceutically acceptable salts thereof, for example, those in which a radioactive isotope such as 3H or 14C is incorporated, are useful in drug and/or substrate tissue distribution studies. Tritiated, i.e., 3H, and carbon-14, i.e., 14C, isotopes are particularly preferred for their ease of preparation and detectability. Further, substitution with isotopes such as deuterium, i.e., 2H, may afford certain therapeutic advantages resulting from greater metabolic stability, for example, increased in vivo half-life or reduced dosage requirements and hence may be preferred in some circumstances. Isotopic variations of the anti-malarial agents and pharmaceutically acceptable salts thereof of this disclosure can generally be prepared by conventional procedures using appropriate isotopic variations of suitable reagents.

Solvates

The aurora kinase inhibitors of the disclosure, such as those disclosed in FIGS. 1-13 and novel agents referred to herein, also include solvate forms of the agents. The terms used in the claims encompass these forms.

Polymorphs

The aurora kinase inhibitors of the disclosure, such as those disclosed in FIGS. 1-13 and novel agents referred to herein, also include their various crystalline forms, polymorphic forms and (an)hydrous forms. It is well established within the pharmaceutical industry that chemical compounds may be isolated in any of such forms by slightly varying the method of purification and or isolation form the solvents used in the synthetic preparation of such compounds.

Prodrugs

Embodiments of the disclosure further include aurora kinase inhibitors of the disclosure, such as those disclosed in FIGS. 1-13 and novel agents referred to herein, in prodrug form. Such prodrugs are generally compounds wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Metabolites

Also falling within the scope of this disclosure are the in vivo metabolic products of the aurora kinase inhibitors of the disclosure, such as those disclosed in FIGS. 1-13. A "metabolite" is a pharmacologically active product produced through metabolism in the body of a specified compound or salt thereof. Such products can result, for example, from the oxidation, reduction, hydrolysis, amidation, deamidation, esterification, deesterification, enzymatic cleavage, and the like, of the administered compound. Accordingly, the embodiments include metabolites of compounds set forth in FIGS. 1-13, and 16 including compounds produced by a process comprising contacting an aurora kinase inhibitor compound of this described herein with a mammal for a period of time sufficient to yield a metabolic product thereof.

Metabolites are identified, for example, by preparing a radiolabelled (e.g., $^{14}C$ or $^{3}H$) isotope of an aurora kinase inhibitor described herein, administering it parenterally in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolites, so long as they are not otherwise found in vivo, are useful in diagnostic assays for therapeutic dosing of the aurora kinase inhibitor compounds described herein.

According to certain embodiments, provided are methods of preventing or treating malaria in a subject or preventing or treating a subject exhibiting a symptom of malaria. Malaria typically produces a string of recurrent attacks, or paroxysms, each of which has three stages—chills, followed by fever, and then sweating. Along with chills, the person is likely to have headache, malaise, fatigue, muscular pains, occasional nausea, vomiting, and diarrhea. Within an hour or two, the body temperature rises, and the skin feels hot and dry. Then, as the body temperature falls, a drenching sweat begins. The person, feeling tired and weak, is likely to fall asleep. A subject exhibiting one, two or more of the foregoing symptoms is considered a subject in need.

Pharmaceutical Compositions

Aspects also provide pharmaceutical compositions comprising one or more aurora kinase inhibitors as are described herein. Aurora kinase inhibitor(s) can be administered to a patient to achieve a therapeutic effect, e.g., active against parasites of malaria and in turn, treating and/or preventing malaria. Pharmaceutical composition embodiments including an aurora kinase inhibitor can comprise, for example, anti-malarial agents, compounds 1, 2, 3, 4, 5, 6, 7, 101, 102, 103, 104, 105, 106, DC-5156, DC-5154 and DC-5146 as set forth above. In certain embodiments, the active agents were identified by a screening method embodiment described herein, which were identified by their activity against *P. falciparum* Dd2 using a SYBR Green I-based fluorescence assay. The compositions can be administered alone or in combination with at least one other agent, such as a stabilizing compound, which can be administered in any sterile, biocompatible pharmaceutical carrier, including, but not limited to, saline, buffered saline, dextrose, and water. The compositions can be administered to a subject alone, or in combination with other therapeutic agents or treatments as described below.

In addition to the active ingredients, these pharmaceutical compositions can contain suitable pharmaceutically acceptable carriers comprising excipients and auxiliaries that facilitate processing of the active compounds into preparations which can be used pharmaceutically. Pharmaceutical composition embodiments can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the subject.

Further details on techniques for formulation and administration can be found in the latest edition of REMINGTON'S PHARMACEUTICAL SCIENCES (Maack Publishing Co., Easton, Pa., which is incorporated herein by reference). After pharmaceutical compositions have been prepared, they can be placed in an appropriate container and labeled for treatment of an indicated condition. Such labeling would include amount, frequency, and method of administration.

Determination of a Therapeutically Effective Dose

The determination of a therapeutically effective dose of aurora kinase inhibitors identified by a screening method herein is well within the capability of those skilled in the art. A therapeutically effective dose refers to that amount of active ingredient which shows activity against malarial parasites. One example is if activities of $IC_{50}$ of <10 µg/ml against *P. falciparum* 3D7 using malaria parasite growth inhibition assays. Therapeutic efficacy and toxicity, e.g., ED50 (the dose therapeutically effective in 50% of the population) and LD50 (the dose lethal to 50% of the population), can be determined by standard pharmaceutical procedures in cell cultures or experimental animals. The dose ratio of toxic to therapeutic effects is the therapeutic index, and it can be expressed as the ratio, LD50/ED50.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Preferably, a therapeutic agent gains access to the parasite or the infected red blood cell for the duration of time necessary for its normal action.

Screening

One embodiment for screening for compounds having activity against malaria includes the SYBR Green I Assay described as follows:

SYBR Green-I Fluorescence Assay

Ten millimolar compound stocks in DMSO were diluted by ½, ⅕, and/or ¹⁄₁₀ fold dilutions in ultrapure water or RPMI 1640. Varying concentrations of compound were added to culture at a 1% parasitemia and 2% hematocrit in 96-well black plates. Assay conditions maintained maximum DMSO concentrations less than 0.125% per dilution. Positive (baseline 0% growth) controls consisted of Chloroquine at 1 µM final concentration. Following 72 h incubation at 37° C. in 5% $CO_2$, dilution plates were frozen at −80° C. for a minimum of 30 minutes. Dilution plates were allowed to thaw followed by lysis treatment and SYBR Green I incorporation. DNA quantification was determined using a fluorescence reading on a Synergy H4 multimode plate reader set at 485 nm excitation and 530 nm emission as previously reported (Roberts, Iyamu et al. 2016). $EC_{50}$ was calculated from a dose response curve that was generated from a concentration range of 0-10 µM using GraphPad Prism v5.0.

Different dilutions of the compound/fraction in 1 µl of the culture medium were added to 99 µl of *P. falciparum* culture at a 1% parasitemia and 2% hematocrit in 96-well plates. Maximum DMSO concentration in the culture never exceeded 0.125%. Chloroquine at 1 µM was used as a positive control to determine the baseline value. Following 72 hours incubation at 37° C., the plates were frozen at −80° C. After thawing, 100 µL of lysis buffer (with SYBR Green I dye 1:10,000) was added to each well and plates were incubated at room temperature for 30 minutes prior to reading.

Symptoms

The compounds and compositions as described herein may be utilized for the treatment or prevention of one or more symptoms of malaria. The signs and symptoms of malaria often begin 8-25 days following infection, but may occur later in those who have taken anti-malarial medications as prevention. Symptoms may include but are not limited to fever, shivering, arthralgia (joint pain), vomiting, hemolytic anemia, jaundice, hemoglobinuria, retinal damage, e.g., retinal whitening, abnormal posture, and convulsions. The classic symptoms of malaria include the cyclical occurrence of sudden coldness, rigor, fever and sweating lasting about two hours or more, occurring every 2-4 days. In some cases, the fever may be continuous. Severe symptoms, which are more likely in the case of *P. falciparum* infection, include splenomegaly (enlarged spleen), severe headache, cerebral ischemia, hepatomegaly (enlarged liver), hypoglycemia, and hemoglobinuria with renal failure.

Conjunctive Therapeutic Agents

In any of the embodiments described above, any of the compound and/or composition embodiments can be co-administered with other appropriate therapeutic agents (conjunctive agent or conjunctive therapeutic agent) or therapies for the treatment or prevention of malaria and/or a symptom thereof. The term "co-administered" or "co-administration" or "co-administers" as used herein means administration of an active agent before, concurrently, or after the administration of another active agent such that the biological effects of either agents overlap. The combination of agents as taught herein can act synergistically to treat or prevent the various diseases, disorders or conditions described herein. Using this approach, one may be able to achieve therapeutic efficacy with lower dosages of each agent, thus reducing the potential for adverse side effects.

Selection of the appropriate conjunctive agents or therapies for use in combination therapy can be made by one of ordinary skill in the art, according to conventional pharmaceutical principles. The combination of therapeutic agents or therapies can act synergistically to effect the treatment or prevention of malaria or a symptom thereof. Using this approach, one may be able to achieve therapeutic efficacy with lower dosages of each agent, thus reducing the potential for adverse side effects.

Exemplary conjunctive agents that may be formulated and/or administered with a compound as described herein include, but are not limited to chloroquine (Aralen), quinine, tetracycline, clindamycin (Cleocin), mefloquin (Lariam), sulfadoxone/pyrimethamine (Fansidar), primaquine and halofantrine. It is appreciated that suitable conjuvant therapeutic agents may also comprise any combinations, prodrugs, pharmaceutically acceptable salts, analogs, and derivatives thereof.

The mode of administration for a conjunctive formulation in accordance with the teachings herein is not particularly limited, provided that the one or more of compounds 1, 2, 3, 4, 5, 6, 7, 101, 102, 103, 104, 105, 106, DC-5156, DC-5154, and DC-5146 as described herein and the conjunctive agent are combined upon administration. Such an administration mode may, for example, be (1) an administration of a single formulation obtained by formulating an aurora kinase inhibitor and a conjunctive agent simultaneously; (2) a simultaneous administration via an identical route of the two agents obtained by formulating an aurora kinase inhibitor and a conjunctive agent separately; (3) a sequential and intermittent administration via an identical route of the two agents obtained by formulating an aurora kinase inhibitor and a conjunctive agent separately; (4) a simultaneous administration via different routes of two formulations obtained by formulating an aurora kinase inhibitor and a conjunctive agent separately; and/or (5) a sequential and intermittent administration via different routes of two formulations obtained by formulating an aurora kinase inhibitor and a conjunctive agent separately (for example, an aurora kinase inhibitor followed by a conjunctive agent, or inverse order) and the like.

The dose of a conjunctive formulation may vary depending on the formulation of the novel anti-malarial agent and/or the conjunctive agent, the subject's age, body weight, condition, and the dosage form as well as administration mode and duration. One skilled in the art would readily appreciate that the dose may vary depending on various factors as described above, and a less amount may sometimes be sufficient and an excessive amount should sometimes be required.

The conjunctive agent may be employed in any amount within the range causing no problematic side effects. The daily dose of a conjunctive agent is not limited particularly and may vary depending on the severity of the disease, the subject's age, sex, body weight and susceptibility as well as time and interval of the administration and the characteristics, preparation, type and active ingredient of the pharmaceutical formulation. An exemplary daily oral dose per kg body weight in a subject, e.g., a mammal, is about 0.001 to 2000 mg, preferably about 0.01 to 500 mg, more preferably about 0.1 to about 100 mg as medicaments, which is given usually in 1 to 4 portions.

When the aurora kinase inhibitor and a conjunctive agent are administered to a subject, the agents may be administered at the same time, but it is also possible that a conjunctive agent is first administered and then an aurora kinase inhibitor is administered, or that an aurora kinase inhibitor is first administered and then a conjunctive agent is administered. When such an intermittent administration is employed, the time interval may vary depending on the active ingredient administered, the dosage form and the administration mode, and for example, when a conjunctive agent is first administered, an aurora kinase inhibitor may be administered within 1 minute to 3 days, preferably 10 minutes to 1 day, more preferably 15 minutes to 1 hour after the administration of the conjunctive agent. When an aurora kinase inhibitor is first administered, for example, then a conjunctive agent may be administered within 1 minute to 1 day, preferably 10 minutes to 6 hours, more preferably 15 minutes to 1 hour after the administration of a novel anti-malarial agent.

It is understood that when referring to an aurora kinase inhibitor and a conjunctive agent, it is meant an aurora kinase inhibitor alone, a conjunctive agent alone, as a part of a composition, e.g., composition, which optionally includes one or more pharmaceutical carriers. It is also contemplated that more than one conjunctive agent may be administered to the subject if desired.

EXAMPLES

Overview

The intraerythrocytic development of the malaria parasite diverges from the paradigm of eukaryotic cell cycle. Novelty of the *Plasmodium* cell cycle offers opportunities for development of therapeutics directed against essential components. Plasmodial kinases, such as Aurora kinases, could prove to be valuable targets for therapies because of their pivotal roles in regulating cell division. Essential *Plasmodium* Aurora-related kinases (Arks) 1, 2, and 3 are homologous to Aurora A and B, Ser/Thr kinases involved in cell division. PfArk-1 has been shown to be expressed during early schizogony. PfArk-2 contains a classical aurora kinase domain similar to that of Aurora A, and PfArk-2 and PfArk-3 have been shown to be expressed during schizogony. To discover potent and selective small molecule inhibitors of PfArks, screening was conducted of a library of optimized mammalian Aurora kinase inhibitors that have evolved from a general pharmacophore models for Ser/Thr kinases. In addition, we are also repurposing human Aurora kinase inhibitors to discover antimalarial lead compounds. Novel potent inhibitors (EC50<1 µM) were identified in cell-based screening using SYBR Green I fluorescence based assay. Selectivity of the hits against mammalian cells were determined using the MTS ((3-(4,5 dimethylthiazol-2-yl)-5-(3-carboxymethoxyphenyl)-2-(4-sulfophenyl)-2H-tetrazolium, inner salt) cell proliferation assay. Results from our studies to assess structure-activity-relationship, specificity of inhibition, and cellular effects of the compounds will be presented.

Example 1: General Ser/Thr Kinases Pharmcocophore Approach for Selective Kinase Inhibitors of Aurora Kinases The pharmacophore elucidating module of MOE (Chemical Computing Group) was used to construct the general pharmacophore model (See FIG. 14). The model pharmacophore resembles a diamond with two opposite hydrophobic center, one aromatic center and 2H-bond donor and acceptor projections. A potential scaffold could be a thiazole group connected through an amino group to a nitrogen-containing 6-member aromatic ring, which is linked to pyrrolidine or piperidine ring.

Figure 15:
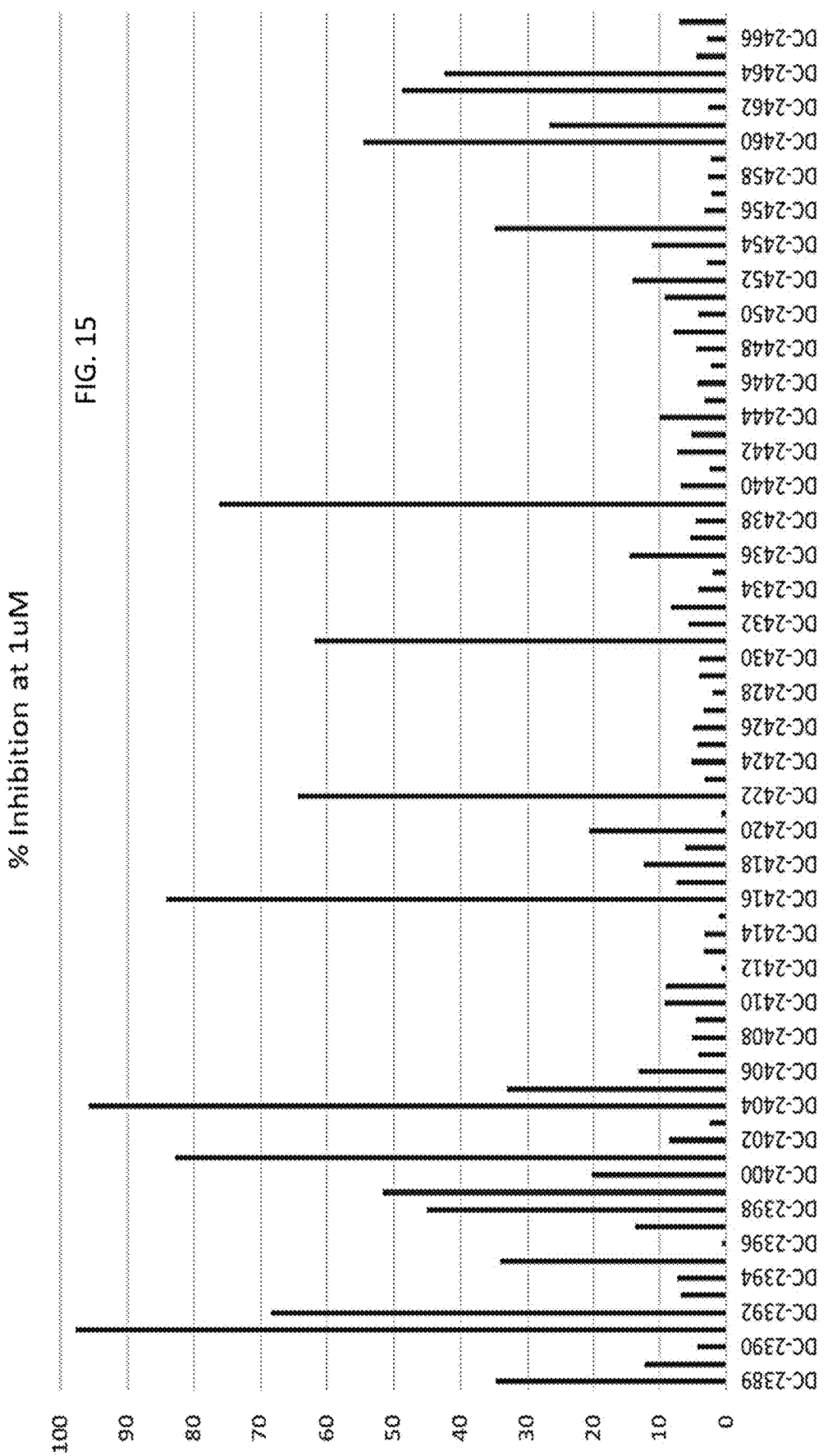
FIG. 15 provides a graph showing screening results for compounds inhibiting intraerythrocytic growth of chloroquine resistant. *P. falciparum* Dd2.
Figure 16:
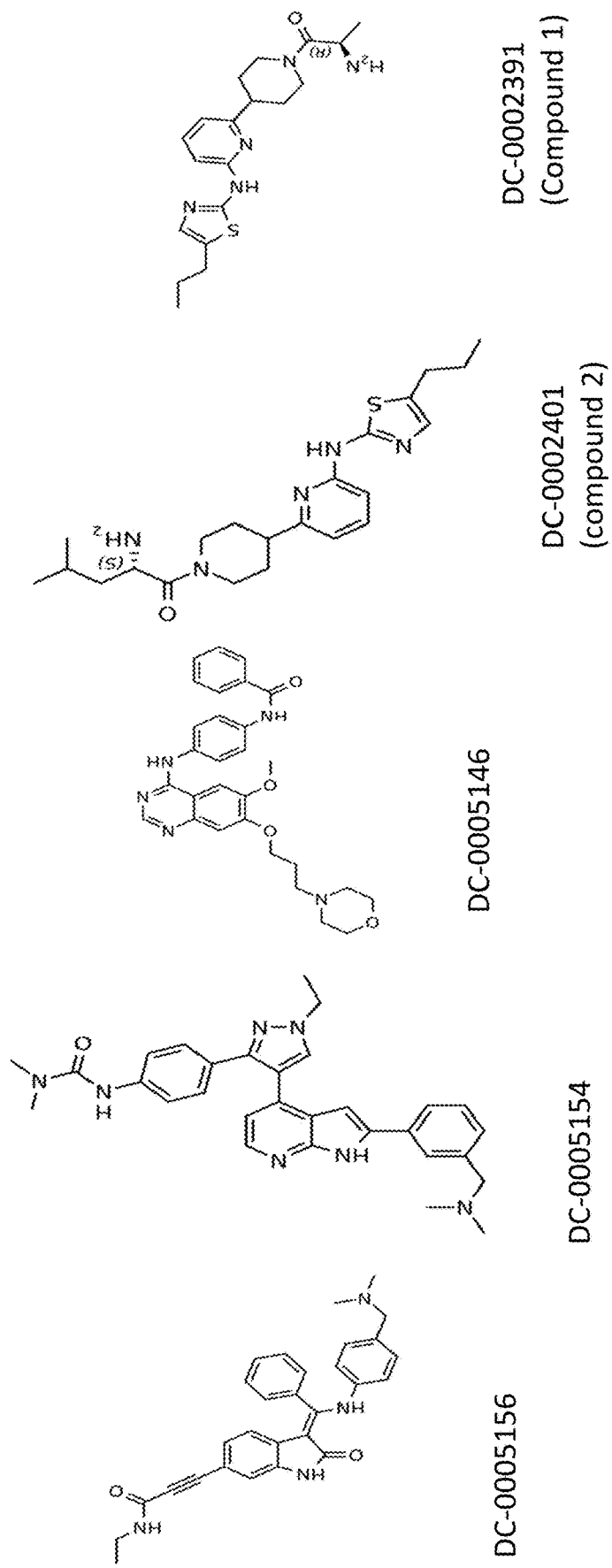
FIG. 16 shows the chemical structures of selected compounds showing inhibition of chloroquine resistant. *P. falciparum* Dd2.

Example 2: Phenotypic Screening of Plasmodium with Aurora Kinase Inhibitors 80 compounds were screened for their ability to inhibit the intraerythrocytic growth of chloroquine-resistant P. falciparum Dd2 using a SYBR Green I-based fluorescence assay [1] at 1 µM. Ten compounds exhibited >50% inhibition as shown in FIG. 15.

7 hit compounds and 17 mammalian Aurora A and B inhibitors in clinical trial were screened by SYBR Green I-based fluorescence assay to determine $IC_{50}$ values in chloroquine-resistant P. falciparum Dd2 and the cytotoxicity was evaluated in 3T3 Mouse fibroblast cells using MTS cytotoxicity assay [2]. The results of the top 2 ASINEX library compounds and 3 commercially available mammalian Aurora A and B inhibitors are shown in Table 1 below with noted structures provided in FIG. 16.

Example 3: Inhibition of PfArk2 Activity

Figure 17B:
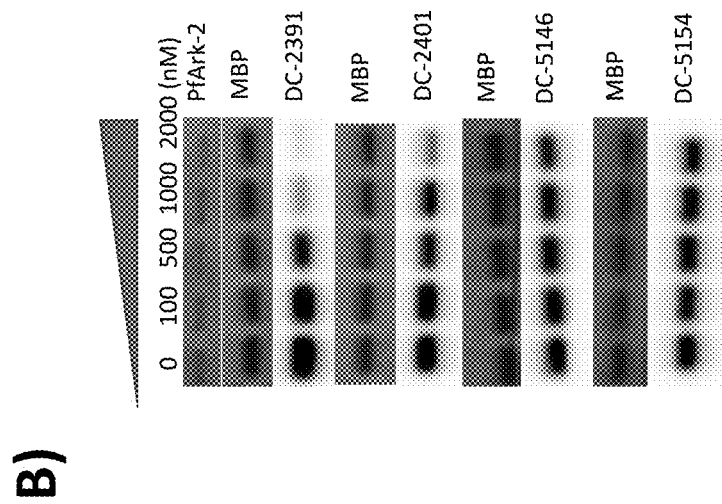
FIG. 17B provides a series of gels showing inhibition of PfArk2 inhibition by compounds that inhibited intraerythrocytic growth of chloroquine resistant. *P. falciparum* Dd2.
Figure 17A:
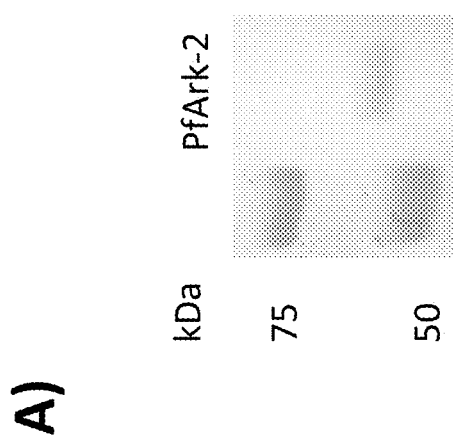
FIG. 17A provides a gel showing purification of PfArk2.

GST-tagged PfArk2 was purified using affinity chromatography (FIG. 17A). Compounds were added to a standard kinase assay at indicated concentrations against PfArk-2 (2.5 µg) in a $\gamma$-$P^{32}$ ATP utilization assay with MBP (2.5 µg) as substrate (FIG. 17B). Upper panels show Coomassie Blue-stained gel and the lower panel is the corresponding autoradiogram. It is evident that Asinex library compounds DC-2391 and DC-2401 (JVH 001 & JVH 003) inhibits PfArk2 activity. In contrast, DC-5146 (BI-847325) and DC-5154 (GSK 1070916) although inhibiting Plasmodium cellular growth was not particularly effective in inhibiting PfArk2 activity. This suggests their cellular targets could be other Plasmodium aurora kinase (Plasmodium falciparum has 3, PfArk1, PfArk2, and PfArk3) or any other kinases.

Figure 18:
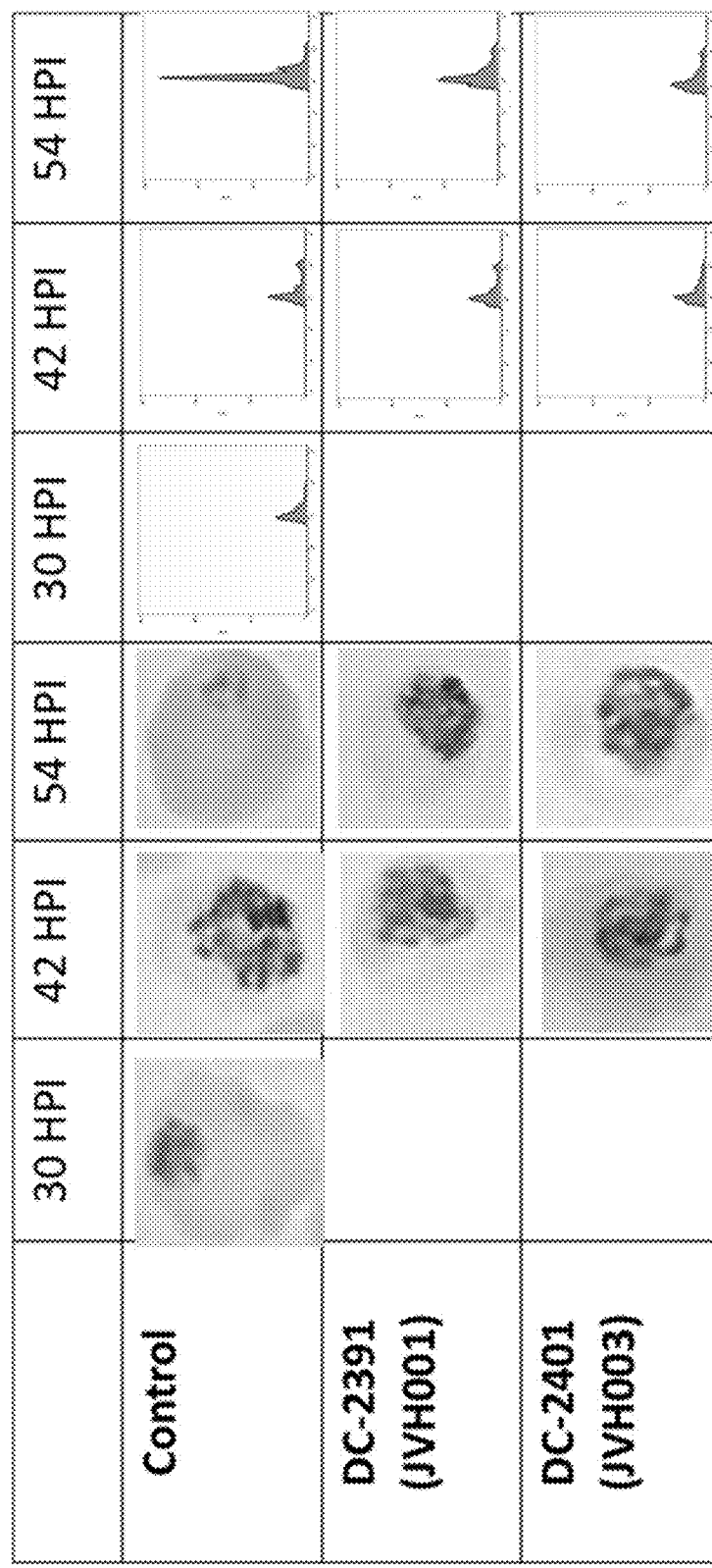
FIG. 18 provides a series of photographs showing that PfArk2 inhibitors block *P. falciparum* at the Schizont stage and flow cytometry analysis of treated cells.

Example 4: PfArk Inhibition Blocks Maturation of Plasmodium at the Schizont Stage The cellular mechanism of action of the most potent compounds were determined by a stage-specific interaction study using synchronized cultures treated with compound at $3 \times IC_{50}$ at 30 hour post invasion (hpi). Slides were taken from treated cultures every 12 hours and stained with Giemsa. Additionally samples were fixed, permeabilized, and stained with YOYO-1 for flow cytometry analysis. As can be seen in FIG. 18, while the control culture matured from the trophozoite stage (30 h post invasion) to the ring stage in the next cell cycle at 54 hpi, the maturation of the inhibitor treated samples was blocked at the schizont stage. This supports that the role of PfArk2 serving as mitotic and cytokinesis regulator similar to mammalian aurora kinases.

Example 5: Phenotypic Effects of Identified Inhibitors

Figure 19:
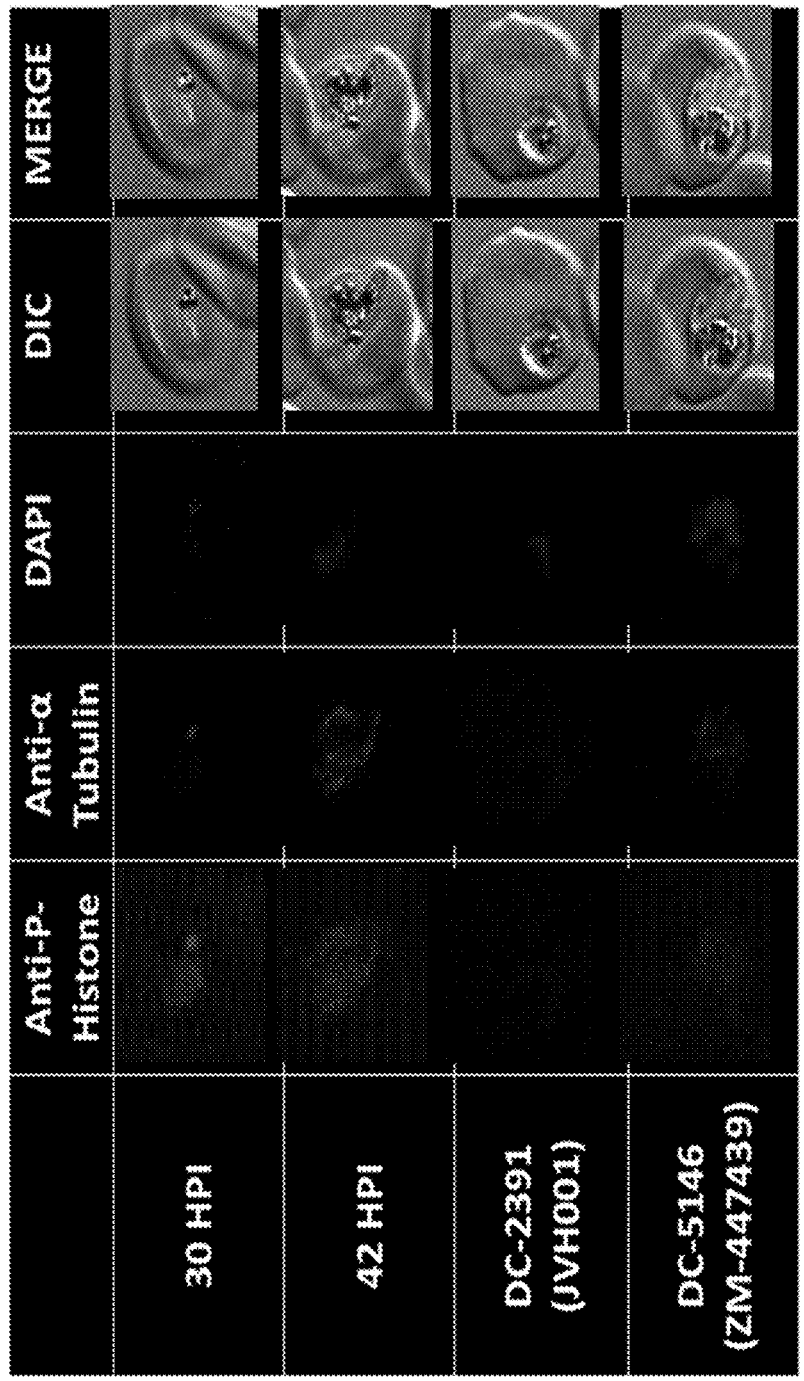
FIG. 19 provides a series of micrographs showing that Aurora kinase inhibitors inhibit histone phosphorylation in *P. falciparum*.

The phenotypic effects of potent compounds were determined by an immunofluorescent assay using synchronized cultures treated with compound at $5 \times IC_{50}$ at 24 hour post invasion (hpi). Cultures were fixed, permeabilized and stained with anti-phospho-histone H3 (Anti-P-Histone), anti-$\alpha$ tubulin (Anti-aTub), and DAPI after 12 hours and visualized via confocal microscopy, see FIG. 19. This figure suggests the role of Plasmodium aurora kinases in histone H3 phosphorylation similar to model organisms as PfArk2 inhibitor DC 2391 (previous JVH001) completely blocks histone phosphorylation as evident from lack of fluorescence staining with anti-phospho-histone antibodies.

It should be borne in mind that all patents, patent applications, patent publications, technical publications, scientific publications, and other references referenced herein and in the accompanying appendices are hereby incorporated by reference in this application to the extent not inconsistent with the teachings herein.

While various embodiments of the present invention have been shown and described herein, it will be obvious that such embodiments are provided by way of example only. Numerous variations, changes and substitutions may be made without departing from the invention herein. Accordingly, it is intended that the invention be limited only by the spirit and scope of the appended claims.

TABLE 1

| Molecule Name | Structure | CDD Number | Former ID | Synonyms | % inhibition (1 µM) | Dd2: IC50 (nM) | Dd2: IC90 (nM) | 3T3: EC50 (nM) | 3T3: EC90 (nM) | Selectivity Index |
|---|---|---|---|---|---|---|---|---|---|---|
| DC-0005156 | | | JVH116 | BI-847325 | 93% | 529.5 | 2005 | 1307 | >26700 | 2.5 |
| DC-0005154 | | CDD-1408484 | JVH114 | GSK-1070916 | 87% | 441.3 | 1720 | 5973.3 | 15866.7 | 13.5 |
| DC-0005146 | | CDD-995693 | JVH106 | ZM-447439 | 75% | 1015.3 | 4315 | 3777.5 | 11700 | 3.7 |
| DC-0002401 | | | JVH003 | LAS 29965976 | 83% | 491.8 | 1565 | 2296.7 | >12000 | 4.7 |
| DC-0002391 | | | JVH001 | LAS 31077790 | 98% | 93.3 | 1788 | 371.4 | 2630 | 4.0 |

REFERENCES

1. Johnson, J. D., et al., *Assessment and continued validation of the malaria SYBR green I-based fluorescence assay for use in malaria drug screening.* Antimicrob Agents Chemother, 2007. 51(6): p. 1926-33.
2. Malich, G., B. Markovic, and C. Winder, *The sensitivity and specificity of the MTS tetrazolium assay for detecting the in vitro cytotoxicity of 20 chemicals using human cell lines.* Toxicology, 1997. 124(3): p. 179-92.

What is claimed is:

1. A method for treating a condition in a subject in need, the method comprising administering to the subject an effective amount of a composition comprising one or more of

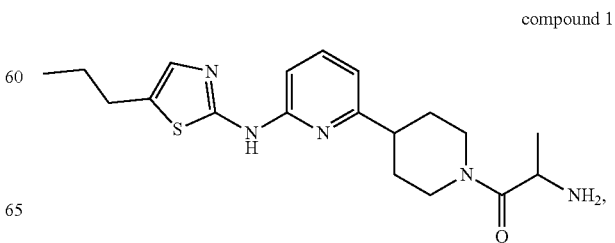

compound 1 compound 2

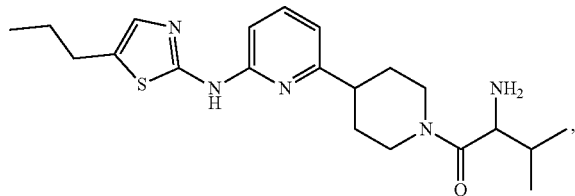

compound 3

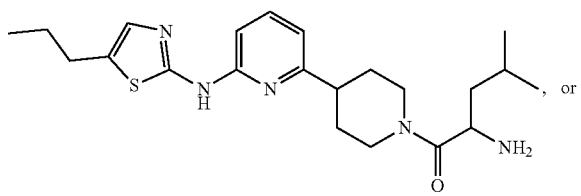

, or compound 7

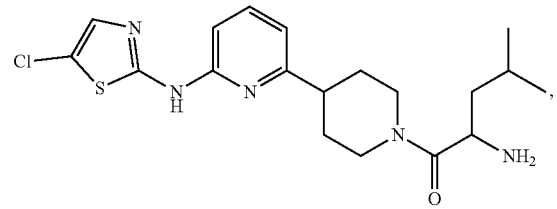

, wherein the condition comprises of a symptom of malaria.

2. The method of claim 1, wherein composition further comprises a pharmaceutically acceptable carrier.

3. The method of claim 1, further comprising co-administering a conjunctive anti-malarial agent to the subject.

4. The method of claim 1, wherein treating malaria comprises killing or arresting the growth of *F. plasmodium* in a subject in need thereof.

\* \* \* \* \*